United States Patent [19]
Herkelmann et al.

[11] Patent Number: 5,434,319
[45] Date of Patent: Jul. 18, 1995

[54] PRODUCTION OF PERFLUOROALKANES

[75] Inventors: Ralf Herkelmann; Werner Rudolph, both of Hanover; Ruediger Sander, Sehnde; Alf Schulz, Neustadt, all of Germany

[73] Assignee: Solvay Fluor und Derivate GmbH, Hanover, Germany

[21] Appl. No.: 220,003

[22] Filed: Mar. 30, 1994

[30] Foreign Application Priority Data

Apr. 3, 1993 [DE] Germany .................. 43 11 062.2

[51] Int. Cl.$^6$ ........................................... C07C 19/08
[52] U.S. Cl. ................................................. 570/123
[58] Field of Search ..................................... 570/123

[56] References Cited

U.S. PATENT DOCUMENTS 2,496,115  1/1950  Burford et al. .
3,686,082  8/1972  Ruehlen .
4,929,317  5/1990  Nishimura et al. .................. 570/123

FOREIGN PATENT DOCUMENTS 271272  6/1988  European Pat. Off. .
2117626  5/1990  Japan .................................. 570/123

OTHER PUBLICATIONS

Haszeldine et al., *J. Chem. Soc.*, 1950:2689–94.
Kirk–Othmer, "*Encyclopedia of chemical Technology*", vol. 10, pp. 840–845, John Wiley & Sons, New York, (1980).

*Primary Examiner*—Alan Siegel
*Attorney, Agent, or Firm*—Evenson, McKeown, Edwards & Lenahan

[57] ABSTRACT

A method for stabilizing and/or purifying perfluoroalkanes, particularly from perfluoroalkanes which contain polyfluoroalkane by-products from their production process, in which the perfluoroalkanes are stabilized and/or purified by reacting the polyfluoroalkane(s) with fluorine at elevated pressure and temperature, to obtain perfluoroalkanes which are substantially free of polyfluoroalkanes. The method has the advantage that the perfluorination takes place rapidly and without significant formation of by-products or decomposition products.

6 Claims, No Drawings

PRODUCTION OF PERFLUOROALKANES

BACKGROUND OF THE INVENTION

The invention relates to a method for the preparation of perfluoroalkanes by reacting mixtures which contain perfluoroalkanes and hydrogen-containing polyfluoroalkanes with elemental fluorine under pressure at elevated temperature.

Perfluorinated organic compounds are chemically very stable, non-combustible, non-toxic and odorless. Due to their high capacity to dissolve oxygen, they are used, inter alia, as blood replacements. They also are useful for other purposes, such as heat-transfer fluids or as solvents. In this case, it is advantageous that the perfluorinated organic material be as free as possible of polyfluorinated compounds, since polyfluorinated compounds may be toxic and do not have the desired stability of perfluorinated organic compounds.

Various methods are known for preparing perfluorinated compounds. Examples include methods based on the exchange of hydrogen atoms for fluorine atoms, e.g. electrofluorination, fluorination with metal fluorides such as $AgF_2$, or reaction with elemental fluorine. In these methods, the starting material may appropriately comprise non-fluorinated or partially fluorinated compounds.

There are various methods for purifying mixtures obtained during such processes which contain perfluorinated and polyfluorinated organic compounds. Reacting the mixtures with strong bases involves loss of material, since the polyfluorinated compounds are destroyed and removed in this process. Processes in which the polyfluorinated compounds are converted into perfluorinated compounds are preferable. For example, U.S. Pat. No. 4,220,606 discloses a method in which hydrocarbons are reacted with silver fluoride, cobalt fluoride or sulfur fluorides in three stages under increasingly severe conditions. In this case, it is also possible in the third stage to start from partially fluorinated material which has been obtained in a different manner. The method is very involved.

U.S. Pat. No. 2,496,115 discloses a method for stabilizing perfluorocarbons in which a mixture of perfluorinated and polyfluorinated compounds is treated with elemental fluorine in order to convert polyfluorinated compounds into perfluorinated compounds. A similar procedure is disclosed in published European patent application No. EP 271,272. In EP 271,272, fluorine, which is optionally diluted with inert gas such as nitrogen, is passed through the mixture to be treated. U.S. Pat. No. 2,496,115 describes in Example 1 that complete perfluorination is only achieved when the reaction temperature is increased from an initial 150° C. to 300° C. Under these conditions, the yield is only 78%.

Despite the efforts of the prior art, there remains a need for better methods of producing perfluoroalkanes free of polyfluoroalkanes.

SUMMARY OF THE INVENTION

It is an object of the present invention to provide an improved method of converting polyfluorinated compounds present in a mixture with perfluorinated compounds into perfluorinated compounds.

Another object of the invention is to provide a method of producing perfluorinated compounds from polyfluorinated materials in a high yield and at a high reaction rate.

These and other objects of the invention are achieved by providing a method of producing a perfluoroalkane substantially free of polyfluoroalkanes in which the method comprises reacting a perfluoroalkane/polyfluoroalkane mixture with a reactive gas consisting essentially of from 40 to 100 vol.-% elemental fluorine and from 0 to 60 vol.-% inert gas at a pressure of from 4 to 12 bar (abs.) and a temperature of from 75° to 120° C.

The invention is based on the discovery that at elevated pressure fluorination of polyfluorinated compounds with elemental fluorine is possible with a high yield, but a low tendency to form by-products.

DETAILED DESCRIPTION OF PREFERRED EMBODIMENTS

The method according to the invention for the preparation of perfluoroalkanes by reacting mixtures which contain perfluoroalkanes and polyfluoroalkanes with a reactive gas selected from the group comprising elemental fluorine and a fluorine/inert gas mixture is characterized in that a reactive gas having a content of 40 to 100% by volume fluorine and 0 to 60% by volume inert gas is used and the reaction is performed at a pressure of 4 to 12 bar (abs.) and a temperature of 75°-120° C. A surprising property of the method according to the invention consists firstly in that much more fluorine can be used than is theoretically necessary for complete exchange of the hydrogen atoms for fluorine atoms. Nevertheless, at best a slight formation of byproducts or decomposition products, for instance by splitting carbon-carbon bonds, is observed. The effectiveness of the method in stabilizing and/or purifying perfluoroalkanes is very high.

As used herein the term "polyfluorinated compounds" refers to fluorinated compounds which contain hydrogen atoms but only to a limited extent. Preferably the ratio of fluorine atoms to hydrogen atoms is 3:1 or higher. Preferred "polyfluorinated compounds" are polyfluorinated alkanes, in particular linear or branched aliphatic alkanes having 3 to 18 carbon atoms with the given minimum ratio of fluorine atoms to hydrogen atoms. Preferred "perfluorinated compounds" are linear or branched perfluorinated aliphatic alkanes with 3 to 18 carbon atoms. Of course, mixtures of such alkanes may also be treated. The preferred inert gas is $N_2$.

It is particularly preferred to use perfluoroalkalne/polyfluoroalkane mixtures which in addition to perfluorinated compounds contain a maximum of 0.5 mole percent of polyfluoroalkane(s).

It has proved advantageous to perform the reaction with a reactive gas consisting essentially of from 40 to 60 volume percent fluorine and from 60 to 40 volume percent inert gas. It has also been found advantageous to carry out the reaction at a pressure of from 5 to 10 bar (abs.) and a temperature of from 80° to 120° C. Preferably the reaction is performed at a temperature of from 80° to 100° C.

When hydrogen is exchanged for fluorine in accordance with the method of the invention, HF is released. The resulting hydrogen fluoride can be separated by conventional methods when working up the reaction product. Preferably the HF which forms is absorbed by means of potassium fluoride or sodium fluoride. It is particularly advantageous to carry out the method of the invention such that the hydrogen-fluorine exchange is performed in the presence of a quantity of an HF adsorption agent, preferably KF or NaF, which is sufficient to adsorb the resulting hydrogen fluoride.

The time required to carry out the method of the invention depends on the desired degree of purification, on the initial content of polyfluorinated compounds, and also on the applied pressure, the temperature used and the relative amount of elemental fluorine. Optimum conditions can be determined by corresponding small-scale tests. Advantageously, the method according to the invention is performed over a period of 5 to 10 hours.

The method according to the invention is particularly suitable for producing or stabilizing linear or branched, aliphatic perfluoroalkanes with 5 to 7 carbon atoms.

In accordance with the method of the invention, perfluoroalkanes which are substantially free of polyfluoroalkanes are produced quickly and with a high yield. They can be used for all those purposes for which such perfluoroalkanes are conventionally used, for instance in the medical field. As used herein, the term "substantially free" denotes a polyfluorocarbon content of less than 100 ppm.

The following examples are intended to illustrate the invention in further detail without restricting its scope.

EXAMPLE 1

Purification of Perfluoroalkanes

Starting material: A mixture having the following composition was used: perfluoropentane approximately 41%; perfluorohexane approximately 42%; perfluoroheptane approximately 16%; polyfluorinated alkanes (hydrogen-containing, not identified further) <0.5% (all percent composition data determined from the relative areas of gas chromatography peaks). Such a mixture can be obtained, for example, by decomposition or rearrangement of the starting compounds or intermediate compounds in electrochemical fluorination of carboxylic acids or by perfluorination of corresponding alkanes by known methods.

One g of NaF was suspended in 200 g of the aforementioned mixture. The suspension was introduced into an autoclave, and 1 bar each of $N_2$ and $F_2$ were applied at room temperature, i.e. the autoclave was pressurized with a reactive gas which contained 50% by volume nitrogen and 50% by volume fluorine. The suspension was then stirred thoroughly for 7 hours at 100° C. and at the autogenous pressure which arose (approximately 5 to 6 bar abs.).

After depressurizing the autoclave, excess reactive gas (which is insoluble in perfluorocarbons) separated from the reaction mixture. Solids (NaF and it addition compounds with HF) were filtered out.

No C—H hydrogen resonances could be detected in the NMR spectrum of the product. Gas-chromatographic analysis of the gas phase yielded a $CF_4$ content of only 0.2 percent (based on the area of the gas chromatogram peak), and no indication of higher homologues as decomposition products.

The example shows that it is possible, substantially without formation of decomposition products, to produce a perfluoroalkane mixture which is substantially free of hydrogen-containing fluorine compounds.

EXAMPLE 2

Purification of Perfluoroalkanes Without the Addition of NaF

Example 1 was repeated, but this time no NaF was added. Results as in Example 1 were obtained. However, hydrogen fluoride was additionally detected in the mixture.

The reaction mixtures may be worked up by adding HF-sequestering agents.

The perfluoroalkane mixtures obtained according to Examples 1 and 2 are suitable, for instance, for use as solvents.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of producing a perfluoroalkane substantially free of polyfluoroalkanes, said method comprising reacting a perfluoroalkane/polyfluoroalkane mixture with a reactive gas consisting essentially of from 40 to 100 vol.-% elemental fluorine and from 0 to 60 vol.-% inert gas at a pressure of from 4 to 12 bar (abs.) and a temperature of from 80° to 100° C.

2. A method according to claim 1, wherein said perfluoroalkane/polyfluoroalkane mixture contains at most 0.5 mole percent polyfluoroalkanes.

3. A method according to claim 1, wherein HF is formed during the reaction of the reactive gas with the polyfluoroalkane(s), and the reaction is carried out in the presence of a sufficient quantity of KF or NaF to absorb essentially all the HF formed during the reaction.

4. A method according to claim 1, wherein said mixture is reacted with a reactive gas consisting essentially of from 40 to 60 vol.-% elemental fluorine and from 60 to 40 vol.-% inert gas at a pressure of from 5 to 10 bar (abs.) and a temperature of from 80° to 100° C.

5. A method according to claim 1, wherein a linear or branched, aliphatic perfluoroalkane having from 5 to 7 carbon atoms is produced.

6. A method according to claim 1, wherein said reacting step is carried out over a period of from 5 to 10 hours.

* * * * *